US012780869B2

(12) United States Patent
Lauber et al.

(10) Patent No.: US 12,780,869 B2
(45) Date of Patent: Nov. 3, 2026

(54) COMPOSITIONS, KITS AND METHODS USEFUL FOR ANALYZING ANTIBODY-CONTAINING SAMPLES

(71) Applicant: Waters Technologies Corporation, Milford, MA (US)

(72) Inventors: Matthew A. Lauber, North Smithfield, RI (US); Xiaoxiao Liu, Natick, MA (US)

(73) Assignee: Waters Technologies Corporation, Milford, MA (US)

( * ) Notice: Subject to any disclaimer, the term of this patent is extended or adjusted under 35 U.S.C. 154(b) by 1077 days.

(21) Appl. No.: 17/592,260

(22) Filed: Feb. 3, 2022

(65) Prior Publication Data

US 2022/0275022 A1 Sep. 1, 2022

Related U.S. Application Data

(60) Provisional application No. 63/154,126, filed on Feb. 26, 2021.

(51) Int. Cl.

*C07K 1/22* (2006.01)
*B01J 20/286* (2006.01)
*B01J 20/32* (2006.01)
*C07K 1/16* (2006.01)

(52) U.S. Cl.

CPC ............... *C07K 1/22* (2013.01); *B01J 20/286* (2013.01); *B01J 20/3219* (2013.01); *B01J 20/3274* (2013.01); *C07K 1/165* (2013.01); *B01J 2220/54* (2013.01)

(58) Field of Classification Search

None

See application file for complete search history.

(56) References Cited

U.S. PATENT DOCUMENTS 5,077,391 A * 12/1991 Raison ................. C07K 16/065 530/808
7,125,517 B2 * 10/2006 Kovalenko ...... G01N 33/54353 435/7.1
2017/0274299 A1 * 9/2017 Coutard .................. C07K 1/36

OTHER PUBLICATIONS

Thermo Fisher Scientific, Inc. Instructions: Sulfo-NHS Acetate, No. 26777 (2013). Found here: https://assets.thermofisher.com/TFS-Assets/LSG/manuals/MAN0011514_SulfoNHS_Acetate_UG.pdf(Year: 2013).*

Pierce. "Protein A IgG Purification Kit" Revision dated: Jan. 2007. Found here: https://www.med.upenn.edu/robertsonlab/assets/user-content/documents/pierce-igg-protein-a-purification-kit.pdf (Year: 2007).*

Amicon. "Amicon Pro Affinity Concentration Kit—Protein G." Revision dated: Feb. 2013. Found here: https://www.sigmaaldrich.com/deepweb/assets/sigmaaldrich/product/documents/102/797/protein-g.pdf?srsltid=AfmBOoqsm8ZJCFHDktkJCOD_F0IIESLJSmO2-x0K_THVhUXVuWNcL2rA (Year: 2013).*

Uptima. "Affinity support for the purification of lgG antibodies." Version referenced published online: Aug. 19, 2021 (via WayBack machine). Found here: https://www.interchim.fr/ft/9/904670.pdf (Year: 2021).*

"GlycoWorks Rapi-Fluor-MS N-Glycan Kit-96 Samples. Care and Use Manual." Waters Corporation. (2017).

"MabSelect SuRe: Affinity Chromatography . Instructions for Use." Cytiva. (2020): 1-32.

Anderson et al. "TNT detection using llama antibodies and a two-step competitive fluid array immunoassay." J. Immunol. Meth. 339(2008): 47-54.

Kim et al. "Evading pre-existing anti-hinge antibody binding by hinge engineering." mAbs. 8.8(2016): 1536-1547.

LOABeads™ Prta: Magnetic bead purificiation of antibodyes. Product Manual. Lab on a Bead. (2018): 1-17.

Muerhoff et al. "Microheterogeneous monoclonal antibody subspecies with differential hepatitis C virus core antigen binding properties identified by SEC-HPLC." J. Immunol. Meth. 345(2009): 60-69.

Ramirez et al. "A Bifunctional Affinity Linker to Couple Antibodies to Cellulose." Biotechnol. 11.13(1993): 1570-1573.

Shivange et al. "A Single-Agent Dual-Specificity Targeting of FOLR1 and DR5 as an Effective Strategy for Ovarian Cancer." Cancer Cell. 34(2018): 331-345.

Zhang et al. "Glycan Residues Balance Analysis—GReBA: A novel model for the N-linked glycosylation of IgG produced by CHO cells." Metab. Eng. 57(2020): 118-128.

* cited by examiner

*Primary Examiner* — Robert A Wax
*Assistant Examiner* — Julia A Rossi
(74) *Attorney, Agent, or Firm* — WOMBLE BOND DICKINSON (US) LLP; Deborah M. Vernon

(57) ABSTRACT

In some aspects, the present disclosure pertains to sample treatment methods that comprise: contacting an acidic elution solution that is free of primary amine, secondary amine and thiol groups with a sorbent having bound target antibody and separating the elution solution from the sorbent, thereby releasing bound target antibody from the sorbent and forming a first collection fraction that comprises the elution solution and released target antibody; contacting the sorbent with a neutralization buffer solution that is free of primary amine, secondary amine and thiol groups and separating the neutralization buffer solution from the sorbent, thereby forming a second collection fraction that comprises the neutralization buffer solution; and forming a neutralized solution that comprises the first collection fraction and the second collection fraction. In other aspects, the present disclosure pertains to kits for performing such sample treatment methods.

18 Claims, 2 Drawing Sheets

COMPOSITIONS, KITS AND METHODS USEFUL FOR ANALYZING ANTIBODY-CONTAINING SAMPLES

CROSS-REFERENCE TO RELATED APPLICATION

This application claims the benefit of U.S. Provisional Application Ser. No. 63/154,126, filed Feb. 26, 2021 and entitled "PROTEIN A PROTOCOL", the disclosure of which is hereby incorporated by reference.

FIELD

The present disclosure pertains to methods of sample treatment in which target antibodies are separated from sample fluid and subjected to additional processing steps, which can include glycan labeling. The present disclosure also pertains to compositions and kits for performing such methods.

BACKGROUND

Affinity chromatography is a well-established method for the capture and purification of biological samples such as immunoglobulins, polyclonal and monoclonal antibodies and antibody fragments. Samples may be, for example, from native or recombinant sources, and may be contained in a variety of sample matrices including, for example, human and animal whole blood, plasma and serum samples, and cell culture supernatants. Common chromatographic sorbents used for isolation and purification by affinity capture include particles to which an affinity capture protein is covalently attached. Common examples include Protein A and Protein G based sorbents which have utility in capturing and purifying samples during drug development, manufacture, and bioanalytical testing.

A typical affinity purification procedure involves multiple steps. For example, the procedure may include a first step in which sorbent particles are washed with a binding buffer that enhances binding of the target analyte to the affinity sorbent. The sample is then introduced and target analytes are bound to the sorbent particles. After binding, the sorbent particles are washed to remove unbound substances while leaving the target analytes bound to the sorbent particles. An elution step is then conducted, commonly at a lower pH, to release and collect the purified target analyte for further measurement and characterization.

Current affinity purification procedures, however, generally produce purified target analyte solutions that contain significant amounts of strong nucleophiles, particularly primary and/or secondary amines, which can interfere with subsequent processing steps, including reactions in which label reagents are reacted with amine-containing analytes, among others. These and other drawbacks of current affinity purification procedures are addressed by the present disclosure.

SUMMARY

In various aspects, the present disclosure provides sample treatment methods that include the following: (a) contacting a sample fluid that contains a target antibody with a sorbent that has affinity for the target antibody and separating the sample fluid from the sorbent, thereby forming a sorbent having bound target antibody; (b) contacting a washing solution with the sorbent having bound target antibody and separating the washing solution from the sorbent having bound target antibody, thereby removing unbound molecules from the sorbent while leaving target antibody bound to the sorbent; (c) contacting an acidic elution solution with the sorbent and separating the elution solution from the sorbent, thereby releasing bound target antibody from the sorbent and forming a first collection fraction that comprises the elution solution and released target antibody, the acidic elution solution being free of strong nucleophiles, specifically, molecules having primary amine groups, secondary amine groups or thiol groups; (d) contacting the sorbent with a neutralization buffer solution and separating the neutralization buffer solution from the sorbent, thereby forming a second collection fraction that comprises the neutralization buffer solution, the neutralization buffer solution being free of strong nucleophiles, specifically, molecules having primary amine groups, secondary amine groups or thiol groups; (e) forming a neutralized solution that comprises the first collection fraction and the second collection fraction, the neutralized solution comprising the released target antibody, the elution solution, and the neutralization buffer solution (note that the second collection fraction can be directly added to the first collection fraction at the time of formation, without separately collecting the second collection fraction as a distinct entity); and (f) subjecting the neutralized solution to additional processing steps that comprise a chemical reaction with an amine-reactive reagent.

In some embodiments, the target antibody is selected from an immunoglobulin, a polyclonal antibody, a monoclonal antibody, multivalent antibody, an antibody fragment, an antibody-drug conjugate, or an oligonucleotide-antibody conjugate.

In some embodiments, which can be used in conjunction with the above aspects and embodiments, the elution solution has a pH ranging from 1 to 5.

In some embodiments, which can be used in conjunction with the above aspects and embodiments, the elution solution is further free of hydroxyl groups.

In some embodiments, which can be used in conjunction with the above aspects and embodiments, the elution solution comprises an organic acid that is selected from carboxylic acids and phosphonic acids.

In some embodiments, which can be used in conjunction with the above aspects and embodiments, the neutralization buffer has a pH ranging from 7 to 14.

In some embodiments, which can be used in conjunction with the above aspects and embodiments, the neutralization buffer is further free of hydroxyl groups.

In some embodiments, which can be used in conjunction with the above aspects and embodiments, the neutralization buffer comprises borate anions.

In some embodiments, which can be used in conjunction with the above aspects and embodiments, the sorbent comprises an affinity ligand selected from proteins, antibodies, aptamers, affimers and peptoids.

In some embodiments, which can be used in conjunction with the above aspects and embodiments, prior to contacting the sample fluid with the sorbent, the method further comprises contacting a binding buffer solution with the sorbent and separating the binding buffer solution from the sorbent, wherein the binding buffer solution is free of primary amine, secondary amine and thiol groups. In some of these embodiments, the binding buffer solution has a pH ranging from 5 to 9, the binding buffer solution is further free of hydroxyl groups and/or the binding buffer comprises an organic acid anion selected from carboxylates and phosphonates.

In some embodiments, which can be used in conjunction with the above aspects and embodiments, the neutralized solution is subjected to additional processing steps that comprise deglycosylating the released target antibody with a deglycosylating enzyme to form a deglycosylated target antibody and released glycans that comprise released glycosylamines; and reacting the released glycans with a labeling reagent to form labeled glycans.

In some embodiments, the target antibody is denatured prior to deglycosylating the target antibody.

In some embodiments, which can be used in conjunction with the above aspects and embodiments, the labeling reagent comprises an MS active moiety, a fluorescent moiety, and a moiety that reacts with the released glycans.

In some embodiments, which can be used in conjunction with the above aspects and embodiments, the method further comprising subjecting the labeled glycans to liquid chromatography to separate the labeled glycans.

In some embodiments, which can be used in conjunction with the above aspects and embodiments, the method further comprises subjecting the labeled glycans to mass spectrometry and/or measuring a fluorescent signal of the labeled glycans.

In other aspects, the present disclosure provides kits for treating a sample fluid that contains a target antibody, the kits comprising the following: (a) a sorbent that has affinity for the target antibody, (b) a device for housing the sorbent, (c) an acidic solution that has a pH ranging from 1 to 5 and is free of primary amine groups, secondary amine groups, thiol groups or a concentrate for forming an acidic solution that is free of primary amine groups, secondary amine groups, thiol groups, (d) a neutralization buffer solution that has a pH ranging from 7 to 14 and is free of primary amine groups, secondary amine groups, thiol groups or a concentrate for forming a neutralization buffer solution that is free of primary amine groups, secondary amine groups, thiol groups, and (e) optionally, a binding buffer solution that is free of primary amine, secondary amine and thiol groups or a concentrate for forming a binding buffer solution that is free of primary amine, secondary amine and thiol groups. In some embodiments, the kits further comprise one or more of the following: (a) a deglycosylating enzyme, (b) a labeling reagent, and (c) a denaturing reagent.

DETAILED DESCRIPTION

Figure 1A:
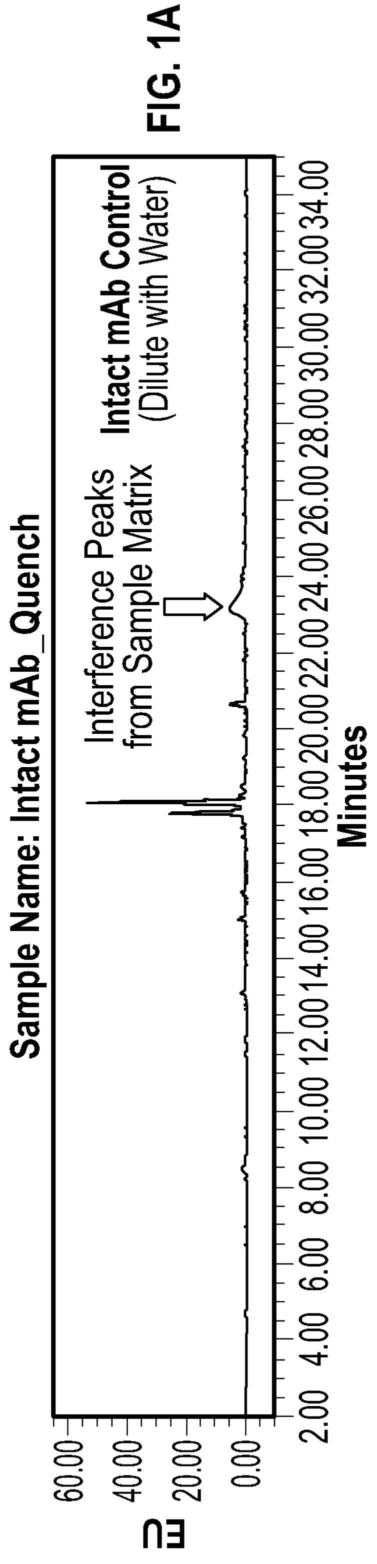
FIG. 1A is a chromatogram showing a glycan profile based on an intact monoclonal antibody (mAb) mass check standard produced without performing Protein A purification.

The present disclosure pertains to methods of treating samples that contain at least one target antibody, including methods in which one or more target antibodies is/are isolated, purified, separated and/or analyzed.

Samples for use in conjunction with the present disclosure include biological fluids such as whole blood, plasma, serum, urine, saliva, wound exudate, cell lysates, cell culture supernatants, and drug formulations, among others.

Target antibodies in the samples may vary broadly and include immunoglobulins, polyclonal antibodies, monoclonal antibodies, including monospecific monoclonal antibodies and multi-specific monoclonal antibodies (e.g., bi-specific monoclonal antibodies, tri-specific monoclonal antibodies, etc.), multivalent antibodies, antibody fragments, antibody-drug conjugates, and oligonucleotide-antibody conjugates, among others.

In the methods of the present disclosure, the sample fluid that contains the at least one target antibody is contacted with a sorbent that has an affinity for the at least one target antibody and the sample fluid, thereby providing a sorbent having bound target antibody. Contact may be made, for example, by flowing the sample fluid through the sorbet or by dispersing the sorbent within the sample fluid. In either case, the sample fluid (now depleted of the at least one target antibody after contact with the sorbent) is separated from the sorbent.

Sorbents having affinity for target antibodies for use in conjunction with the present disclosure include sorbents that comprise an affinity ligand selected from proteins, antibodies, aptamers, affimers and peptoids. Particular examples of sorbents having affinity for target antibodies include sorbents that comprise an affinity ligand selected from Protein A, Protein G, Protein L, Protein A/G, Protein A/G/L, jacalin, and engineered homologs of the same. Sorbents for use in conjunction with the present disclosure include those that comprise a solid support, which may be selected from an inorganic material such as silica, an organic material such as a polymer, or a hybrid organic-inorganic material. Polymers many include crosslinked agarose, cellulose, dextran, polyacrylamide, polymethacrylate, polymethylmethacrylate, or a copolymer comprising a hydrophobic monomer (e.g., divinylbenzene, styrene, etc.) and a hydrophilic monomer (e.g., vinyl pyrrolidone, N-vinyl caprolactam, etc.).

The sorbent can be disposed in a suitable separation device during contact with the sample fluid and other fluids described herein (i.e., washing solution, elution solution, neutralization buffer solution, optional binding buffer solution). There are a number of device formats that can be used in the methods of the present disclosure. Devices include dispersive devices and flow through devices.

In a dispersive device, the sample fluid and other fluids described herein can be slurried with the sorbent particles and allowed to equilibrate. Agitation may be supplied by shaking, stirring, or capping/inverting the device for the required time, after which the sorbent particles and fluid can be separated before proceeding to the next step. Separation is generally achieved by filtration (which may be assisted by gravity, positive pressure or suction), by centrifugation or, if magnetic sorbent beads are used, by drawing the beads towards a magnet and removing the liquid portion. An advantage of the dispersive approach is that the contact time during binding, washing and elution can be easily controlled.

Flow through devices can be viewed as small scale chromatographic columns in which the sample fluid and other fluids described herein are flowed through the devices, in which the sorbent is contacted with and separated from the sample fluid and other fluids described herein in a single step. The sample fluid and other fluids described herein may be pumped through the flow through devices at predetermined flow rates. The flow rate can be controlled to accommodate binding, washing, and elution kinetics, which are typically time dependent. An advantage of such devices they allow for efficient sample elution using a relatively small volume of elution fluid. Low elution fluid volumes are advantageous for increasing purified sample concentration for further analysis or processing.

Separation devices commonly include a housing having a chamber for accepting and holding the sorbent. In various embodiments, the housing may be provided an inlet and an outlet. Construction materials for the housing include inorganic materials, for instance, metals such as stainless steel and ceramics such as glass, as well as synthetic polymeric materials such as polyethylene, polypropylene, polyether ether ketone (PEEK), or polycarbonate.

In certain embodiments, the device may include one or more filters which act to hold the sorbent in a housing. Exemplary filters may be, for example, in a form of a membrane, screen, frit or spherical porous filter.

In some embodiments, a sample fluid or other solution (e.g., a washing solution, elution solution, neutralization buffer solution, etc.) received in the housing may flow into the sorbent spontaneously, for example, via capillary action. Alternatively, the flow may be generated through the sorbent by external forces, such as gravity or centrifugation, or by applying a vacuum to an outlet of the housing and/or positive pressure to an inlet of the housing.

Specific examples of devices for use in the present disclosure include, for example, a syringe, an injection cartridge, a column (e.g., a microbore column, capillary column or nanocolumn), a multi-well device such as a 4 to 8-well rack, a 4 to 8-well strip, a 48 to 96-well plate, a 96 to 384-well micro-elution plate, micro-elution tip devices, including a 4 to 8-tip micro-elution strip, a 96 to 384-micro-elution tip array, a single micro-elution pipet tip, a thin layer plate, a microliter plate, a spin tube or other spin container. Multi-well formats are commonly used with robotic fluid dispensing systems. Typical multi-well formats include 48-, 96-, and 384-well standard plate formats, although other formats are clearly possible.

As previously indicated, in the methods of the present disclosure, a sample fluid that contains at least one target antibody is contacted with a sorbent that has an affinity for the at least one target antibody, and the sample fluid separated from the sorbent, thereby providing a sorbent having bound target antibody (and sample fluid that is depleted of the at least one target antibody). This step may also be referred to herein as a loading step.

After the loading step, a washing solution is contacted with the sorbent having bound target antibody and the washing is separated from the sorbent, thereby removing unbound molecules from the sorbent while leaving target antibody bound to the sorbent. The washing solution is free of strong nucleophiles, in particular, molecules having primary amine groups, secondary amine groups or thiol groups. In various embodiments, the washing solution is also free of weak nucleophiles, in particular, molecules having hydroxyl groups. Suitable washing solutions include water and aqueous buffers comprised of 1 to 200 mM buffering agent with pH values ranging from 5 to 10.

After at least one such washing step is performed, the sorbent is contacted with an acidic elution solution, and the acidic elution solution is separated from the sorbent. Contact with the acidic elution solution results in release of bound target antibody from the sorbent, and a collection fraction is formed that comprises the elution solution and released target antibody.

The acidic elution solution has a pH ranging from 1 to 5, and more typically a pH ranging from 2 to 4. The acidic elution solution is free of strong nucleophiles, in particular, molecules having primary amine groups, secondary amine groups or thiol groups. In some embodiments, the acidic elution solution is also free of weak nucleophiles, in particular, molecules having hydroxyl groups.

In particular embodiments, the elution solution contains at least one organic acid that is free of primary amine groups, secondary amine groups and thiol groups, and which may further be free of hydroxyl groups. The at least one organic acid may be present, for instance, in a concentration ranging from 0.005 M or less to 0.5 M or more, for example, ranging anywhere from 0.005 M to 0.01 M to 0.025 M to 0.05 M to 0.1 M to 0.25 M to 0.5 M (in other words, ranging between any two or the preceding numerical values).

Organic acids may be selected, for example, from carboxylic acids and phosphonic acids. Examples of carboxylic acids include formic acid, acetic acid, difluoroacetic acid, trifluoroacetic acid, propionic acid, butyric acid, oxalic acid, malonic acid, succinic acid, maleic acid, glutaric acid, and citric acid. Examples of phosphonic acids include etidronic acid and medronic acid.

After at least one such eluting step is performed, a neutralization step is performed by contacting the sorbent with a neutralization buffer solution, and the neutralization buffer solution is separated from the sorbent, thereby forming a collection fraction that comprises the neutralization buffer solution.

The neutralization buffer solution has a pH ranging from 7 to 14, more typically a pH ranging from 8 to 12. The neutralization buffer solution is free of strong nucleophiles, in particular, molecules having primary amine groups, secondary amine groups or thiol groups. In some embodiments, the neutralization buffer solution is also free of weak nucleophiles, in particular, molecules having hydroxyl groups.

In particular embodiments, the elution solution contains borate anions, is free of primary amine groups, secondary amine groups and thiol groups, and may further be free of hydroxyl groups. The borate anions may present in a concentration ranging from 0.05 M or less to 2 M or more, for example ranging anywhere from 0.05 M to 0.1 M to 0.25 M to 0.5 M to 1.0 M to 2.0 M. In addition to borate anions, the neutralization buffer also comprises a suitable cations, such as Group IA metal cations (i.e., lithium, sodium, potassium, etc.), tertiary amine cations, or quaternary amine cations.

In certain embodiments, the neutralization buffer is also free of phosphate anions.

After at least one such neutralization step is performed, a neutralized solution that comprises purified target antibody is formed by combining: (a) the collection fraction(s) from the elution step(s), which comprise(s) acid elution solution and released target antibody, and (b) the collection fraction (s) from the neutralization step(s), which comprise(s) neutralization buffer solution. This neutralized solution is then subjected to additional processing steps that may comprise a chemical reaction with an amine-reactive reagent as described further below.

In some embodiments, before contacting the sample fluid with the sorbent, the sorbent is optionally pre-treated by contacting the sorbent with a binding buffer solution. The binding buffer solution may have a pH ranging from 5 to 9, more typically a pH ranging from 6 to 8. The binding buffer solution is free of strong nucleophiles, in particular, molecules having primary amine groups, secondary amine groups or thiol groups. In some embodiments, the binding buffer solution is also free of weak nucleophiles, in particular, molecules having hydroxyl groups.

In particular embodiments, the binding buffer solution contains one or more organic acid anions that is/are free of primary amine groups, secondary amine groups and thiol groups, and which may further be free of hydroxyl groups. The one or more organic acid anions may present in a concentration ranging from 1 mM to 1000 mM, more typically between 2 mM and 200 mM. Organic acid anions may be selected, for example, from carboxylic acid anions and phosphonic acid anions. Examples of carboxylic acid anions include formate, acetate, difluoroacetate, trifluoroacetate, propionate, butyrate, oxalate, malonate, succinate, maleate, glutarate and citrate anions. Examples of phosphonic acid anions include etidronate and medronate anions.

As previously noted, the above-described treatment method results in a neutralized solution that contains purified target antibody. Because this neutralized solution is free of strong nucleophiles (other than those that may be present in the purified target antibody), it is useful in subsequent procedures in which a step of performing a chemical reaction with an amine-reactive reagent is performed.

One example of such a subsequent procedure is one in which the neutralized solution is subjected to additional processing steps that comprise deglycosylating the target antibody with a deglycosylating enzyme to form a deglycosylated target antibody and released glycans, including released glycosylamines; and reacting the released glycans with a labeling reagent to form labeled glycans, including labeled glycosylamines.

In various embodiments, the deglycosylating enzyme is an endoglycosidase. Examples of endoglycosidases include PNGase F and PNGase A, among others.

Prior to deglycosylating the target antibody, the target antibody may be denatured by subjecting the target antibody to appropriate denaturing conditions. Such conditions may be established, for example, by the addition of a suitable denaturing agent, examples of which include urea, guanidine, surfactants and solvents such as methanol, acetone, 2-propanol, acetonitrile and the like. Denaturing conditions can also be achieved by elevating temperature. Temperature can be used along with one or more suitable denaturing agents to achieve a combined effect.

In an embodiment, the denaturing agent comprises a mass spectrometry ("MS") compatible surfactant, otherwise referred to as a "cleavable surfactant." Cleavable surfactants are rendered inactive by cleavage, often under acidic conditions, in order to selectively remove the cleavage product. One example of a cleavable surfactant is the acid-labile anionic surfactant sodium 3-[(2-methyl-2-undecyl-1,3-dioxolan-4-yl)methoxy]-1-propanesulfonate (also known as "ALS"). ALS can degrade rapidly at low-pH conditions and eliminates surfactant-caused interference. The acid-labile property of ALS can enable sample cleanup prior to MS analysis, often without compromising the quality of the analysis. ALS is marketed by Waters Corporation (Millford MA, USA) as the product RapiGest™ SF (also referred to sometimes as RapiGest surfactant) Other acid-labile surfactants are described in U.S. Pat. No. 8,232,423. Other types of surfactants can be used in the present disclosure which are not acid labile include products such as Invitrosol (IVS), a homogeneous surfactant, sodium deoxycholate ("SDC"), Protease MAX™, the brand name for sodium 3-((1-(furan-2-yl)undecyloxy)carbonylamino) propane-1-sulfonate, n-octyl glucoside ("OG"), Triton X-100, 3-[(3-cholamidopropyl)dimethylammonio]-1-propanesulfonate ("CHAPS") and sodium dodecyl sulfate ("SDS").

After releasing glycans from the target antibody, the released glycans can be reacted with a suitable labeling reagent. In some embodiments, the labeling reagent comprises an MS active moiety, a fluorescent moiety, and a reactive moiety that reacts with the released glycans.

In some embodiments, the MS active moiety of the labeling reagent may be a tertiary or quaternary amino group or other MS active group, which can be analyzed using mass spectrometry. Particular examples of mass spectrometry include electrospray ionization mass spectrometry (ESI-MS), matrix-assisted laser desorption/ionization mass spectrometry (MALDI-MS), and time-of-flight mass spectrometry (TOFMS), among others.

In some embodiments, the fluorescent moiety of the labeling reagent may be a fluorescent heterocyclic aromatic moiety, a florescent carbocyclic aromatic moiety or other fluorescent moiety. Fluorescence occurs when certain molecules absorb light at specific wavelengths, promoting the molecules to a higher energy state. As they return to their normal energy states, the "excited" molecules release their absorbed energy as photons. Fluorescence can be measured, for example, with a scanning fluorescence detector, which illuminates a sample with high-intensity light after which the detector then measures the low levels of fluorescence emitted by the sample. The emitted light is typically filtered, amplified, and converted to electrical signals that can be recorded and analyzed.

In some embodiments, the reactive moiety of the labeling reagent that can react with released glycans may be selected from isocyanates, isothiocyanates, succinimidyl esters, succinimidyl carbamates, carboxylic acids, amines, aldehydes, esters, dienes, alkenes and alkynes, among others.

In some embodiments, the labeling reactive moiety that reacts with the released glycans is a moiety that reacts with primary and/or secondary amine groups that are present on released glycosylamines. In certain beneficial embodiments, the reactive moiety may be selected, for example, from an isocyanate moiety, a thioisocyanate moiety, a succinimidyl ester moiety, or a succinimidyl carbamate moiety, among others.

In some embodiments, the labeling reactive moiety that reacts with the released glycans is a moiety that reacts with aldehyde groups and/or ketone groups that are present on released glycans. In certain beneficial embodiments, the reactive moiety may be an amine group. The amine group can provide effective labeling of glycans through reductive amination.

Particular examples of labeling reagents include RapiFluor-MS™ (Waters Corporation), Instant Procaine (InstantPC™) (Prozyme, Inc., Hayward, CA, USA), and Instant AB™ (Prozyme, Inc.).

Because the preceding process steps are performed to ensure that that strong nucleophiles (other than those that are present on the released glycosylamines) are largely or completely absent, there is little unwanted competition for the desired reaction between the labeling reagent and the glycans.

In various embodiments, the methods of the present disclosure comprise subjecting the labeled glycans to liquid chromatography to separate the labeled glycans. Suitable types of liquid chromatography include reversed-phase chromatography and hydrophilic-interaction chromatography (HILIC).

Reversed-phase chromatography generally comprises the use of a polar mobile phase, for example, water or mixtures of water or buffer with polar solvents such as methanol, acetonitrile, isopropanol, or tetrahydrofuran, and a non-polar stationary phase, for example, a hydrocarbon bonded to a silica (e.g., SunFire™ C8 or C18 columns or Symmetry™ C8 or C18 columns available from Waters Corporation) or to a hybrid material (e.g., XBridge™ BEH C8 or C18 columns, or XTerra™ C8, C18 and phenyl columns available from Waters Corporation). In some embodiments, mixed-mode, reversed-phase chromatography separation may be employed, in which case the stationary phase may be an ion exchanger, for example, reversed-phase/anion exchange (AX) column (e.g., Atlantis™ Premier BEH C18 AX columns available from Waters Corporation). Gradient methods employed in reversed-phase chromatography generally move progressively from higher aqueous content, including 100% aqueous content, to lower aqueous content (or viewed conversely, from lower organic content, including 0% organic content, to higher organic content). In mixed mode separations, there is also typically a gradient in buffer concentration and/or pH.

Hydrophilic-interaction chromatography (HILIC) can be viewed as an extension of normal-phase chromatography into the realm of aqueous mobile phases. The mobile phases are generally mixtures of water or buffer (<40%) with polar organic solvents. A typical mobile phase includes acetonitrile (ACN) with a small amount of water. However, any aprotic solvent miscible with water may be used as a polar aprotic solvent, including acetonitrile, acetone, tetrahydrofuran, methylene chloride, ethyl acetate, N,N-dimethylformamide, dimethyl sulfoxide, dioxane and dimethyl ether, among others. The stationary phases are generally very hydrophilic polar stationary phases such as silica, polar bonded phases, polar polymeric phases, and ion exchangers (for example, mixed mode separations, where the HILIC separation also include an anion exchange retention mechanism), examples of such hydrophilic polar stationary phases include members of the Atlantis, CORTECS™, XBridge and ACQUITY™ product families from Waters Corporation. A common feature of all of these stationary phases is that they can easily adsorb water, hence the categorization of "hydrophilic". Gradient methods employed in HILIC mode are generally the opposite of those employed in reversed-phase mode, with initial conditions generally comprising high organic content, typically around 95% organic content, and moving progressively to higher aqueous content. In mixed mode separations, there is also typically a gradient in buffer concentration and/or pH.

In various embodiments, the methods of the present disclosure further comprise additional processing of the eluent from the chromatographic column, for example, to identify, quantify, or otherwise process the nucleic acid component compounds. In some embodiments, mass spectrometry (MS) analysis is performed on the eluent. In some embodiments, fluorescence analysis is performed on the eluent. Alternatively or in addition, the eluent may be subjected to other analytical techniques including infrared analysis, ultraviolet analysis, and nuclear magnetic resonance analysis, among others.

Other embodiments of the present disclosure pertains to kits for treating a sample fluid that contains at least one target antibody. The kits may comprise: (a) a sorbent that has affinity for the target antibody, which may be selected from those described above among others, (b) a device for housing the sorbent, which may be selected from those described above among others, (c) an acidic elution solution, which may be selected from those described above among others, or a concentrate, such as a liquid concentrate or powder, for forming such an acidic elution solution, and (d) a neutralization buffer solution, which may be selected from those described above among others, or a concentrate, such as a liquid concentrate or powder, for forming such a neutralization buffer solution. In some embodiments, the kits may further comprise one or more of the following: (e) a deglycosylating enzyme, which may be selected from those described above among others, (f) a labeling reagent, which may be selected from those described above among others, and (g) a denaturing reagent, which may be selected from those described above among others.

Example 1

Glycoprotein Purification and Enrichment

The following solutions are used in Example 1:
Binding buffer: water or 20 mM sodium acetate, pH 7.4
Wash buffer: water
Elution buffer: 1% acetic acid
Neutralization buffer: 50 mM sodium borate, pH 9
The following purification steps are used in Example 1:
- Condition Protein A wells (UniMab™ 50, Suzhou Nanomicro Technology Co., Ltd., Suzhou, China) with 400 μL of binding buffer. Drive flow with positive pressure manifold (~1.5 psi). Repeat 2 times.
- Load sample containing Intact mAb Mass Check Standard (Waters Corporation) (e.g., for 2 mg protein at 0.1 mg/mL):
  - Attach protein A plate with a new collection plate, load 400 μL of protein solution, and mix well by aspiration.
  - Incubate at room temperature for 4 min, with shaking at ~650 rpm.
  - If there is breakthrough solution in collection plate, transfer back to protein A plate, then drive flow with positive pressure manifold.
  - If needed, collect flow through fraction to check the binding efficiency of plate. Otherwise, discard flow through fraction.
  - Repeat preceding steps, as needed, until all sample has been loaded on plate.
- Wash protein A plate using 400 μL of water. Drive flow with positive pressure manifold. Repeat 2 times.
- Elute captured mAb:
  - Attach protein A plate with a new collection plate, elute mAb from plate by adding 50 μL of 1% acetic acid, and mix well by aspiration.
  - Drive flow with positive pressure manifold.
  - Keep the same collection plate, repeat the preceding two steps.
  - Keep the same collection plate, add 200 μL of neutralization buffer, and drive flow with positive pressure manifold.
  - Save elution fraction from collection plate as the enriched mAb sample. Check protein concentration if needed.

Example 2

Sample Preparation Using Enriched Glycoprotein

The following procedure is used in this example for rapid deglycoslation of the enriched mAb sample:
- Prepare a buffered solution of 5% (w/v) RapiGest (available from Waters Corporation) by dissolving the contents of 1 vial (3 mg) of RapiGest in 60 μL of 5× GlycoWorks™ Rapid Buffer. Vortex to mix.

Transfer 15 μg of protein A enriched mAb solution into a 1 mL tube.

Add 6 μL of buffered solution containing 5% (w/v) RapiGest SF. Aspirate and dispense to mix well.

Add 18.2 MΩ water into a 1 mL tube to bring the total volume of sample mixture to 28.8 μL, mix by aspiration and dispensing.

Transfer this 1 mL tube to pre-heated heating blocks at least 90° C. Heat denature this mixture for 3 minutes. Ensure that the solution temperature is kept at no less than 90° C. during denaturation.

Remove the 1 mL tube from the heat block, allowing the mixture solution to cool for 3 minutes.

Add 1.2 μL of GlycoWorks Rapid PNGase F enzyme solution (available from Waters Corporation). Aspirate and dispense to mix.

Incubate the mixture at another pre-heated heating block at 50° C. for 5 minutes. Maintain the solution temperature at 50° C. during digestion.

Remove the 1 mL tube from the heat block, allowing the resulting deglycosylation mixture to cool at room temperature for 3 minutes.

The following procedure is used in this example for rapid labeling of glycosylamines produced by the prior deglycoslation procedure:

Prepare labeling reagent during the incubation step for deglycosylation. Add 131 μL of the GlycoWorks reagent solvent anhydrous DMF (available from Waters Corporation) to dissolve one vial of 9 mg RapiFluor-MS reagent. Aspirate and dispense the solution 5-10 times to ensure the reagent is fully dissolved. Alternatively, cap and briefly shaking the contents of the reagent vial by hand.

Add 12 μL of the freshly prepared RapiFluor-MS reagent solution (available from Waters Corporation) to the delycosylation mixture in 1 mL tube.

Aspirate and dispense the reagent solution 5 times to ensure mixing.

Allow the labeling reaction to proceed at room temperature for 5 minutes.

Quench the remaining RapiFluor-MS reagent by adding 5 μL of 1M Ammonium Acetate (pH ~7) to the sample mixture. Allow the quench reaction to proceed at room temperature for 5 minutes.

Dilute the quenched sample mixture with 358 μL of acetonitrile in preparation for HILIC solid phase extraction (SPE) clean-up.

The following procedure is used in this example for HILIC SPE clean-up of labeled glycosylamines from the prior rapid labeling procedure:

Prepare solutions used for HILIC SPE clean-up:
  Equilibrating solution: 15:85 water/acetonitrile (v/v)
  Washing solution: 1:9:90 formic acid/water/acetonitrile (v/v/v)

Set up a GlycoWorks HILIC μElution™ plate (available from Waters Corporation) with the waste tray on a vacuum manifold (with a vacuum setting of 2.5-4 Hg to drive flow through). Alternatively, a positive pressure manifold can be used for the SPE clean-up step (with approximately 3 psi).

Condition wells to be used on the μElution plate with 200 μL of 18.2 MΩ water.

Equilibrate wells with 200 μL of 15:85 water/acetonitrile (v/v) solution.

Load the entire ~400 μL acetonitrile diluted samples on the conditioned wells.

Wash the well with two 600 μL volumes of 1:9:90 formic acid/water/acetonitrile (v/v/v).

Replace the waste tray with a 96-well collection plate.

Elute glycans with three 30 μL volumes of GlycoWorks SPE elution buffer (available from Waters Corporation) (200 mM ammonium acetate in 5% acetonitrile).

Save the SPE eluate for liquid chromatographic-fluorescent-mass spectrometry (LC-FLR-MS) analysis

Example 3

Liquid Chromatographic Separation, Fluorescence Analysis and Mass Spectrometry Analysis The following conditions are used for liquid chromatographic (LC) separation, fluorescence (FLR) analysis and mass spectrometry (MS) analysis of post-clean-up RapiFluor-MS labeled glycans from Example 2 above:

TABLE 1

LC-FLR Conditions.

| | |
|---|---|
| LC System: | ACQUITY UPLC ™ H-Class Bio System (Waters Corporation) |
| Column: | ACQUITY Glycan BEH C18 AX 1.7 μm 2.1 × 150 mm Column (Waters Corporation) |
| Sample Temperature | 8° C. |
| Sample Injection Volume: | 1 μL |
| FLR Wavelengths: | 265 Ex/425 Em (RapiFluor-MS-labeled glycans) |
| Column Temperature: | 60° C. |
| Seal Wash: | 70% ACN/30% 18.2 MΩ water v/v (Seal Wash interval set to 5 min) |
| Mobile Phase A: | 18.2 MΩ water |
| Mobile Phase B: | 100 mM ammonium formate, 100 mM formic acid in 40% 18.2 MΩ water/60% acetonitrile (v/v) |
| Active Preheater: | Enabled |
| Scan Rate: | 10 points/sec |

| | Time (min) | Flow (mL/min) | % A | % B | Curve |
|---|---|---|---|---|---|
| 45 min LC Gradient: | 0.0 | 0.4 | 100 | 0 | Initial |
| | 36.0 | 0.4 | 78 | 22 | 6 |
| | 36.3 | 0.4 | 0 | 100 | 6 |
| | 37.3 | 0.4 | 0 | 100 | 6 |

TABLE 1-continued

| LC-FLR Conditions. | | | | |
|---|---|---|---|---|
| 38.0 | 0.4 | 100 | 0 | 6 |
| 45.0 | 0.4 | 100 | 0 | 6 |

TABLE 2

| MS Conditions. | |
|---|---|
| MS System: | Waters Xevo ™ G2-XS QTof |
| Ionization Mode: | ESI, Positive |
| Acquisition Range: | 300-3000 Da |
| Capillary Voltage: | 2.2 kV |
| Source Offset: | 50 V |
| Collision Energy: | Off |
| Cone Voltage: | 75 V |
| Desolvation Gas: | 600 L/hr |
| Source Temperature: | 120° C. |
| Desolvation Temperature: | 500° C. |
| Scan Rate: | 2 Hz |

Figure 1B:
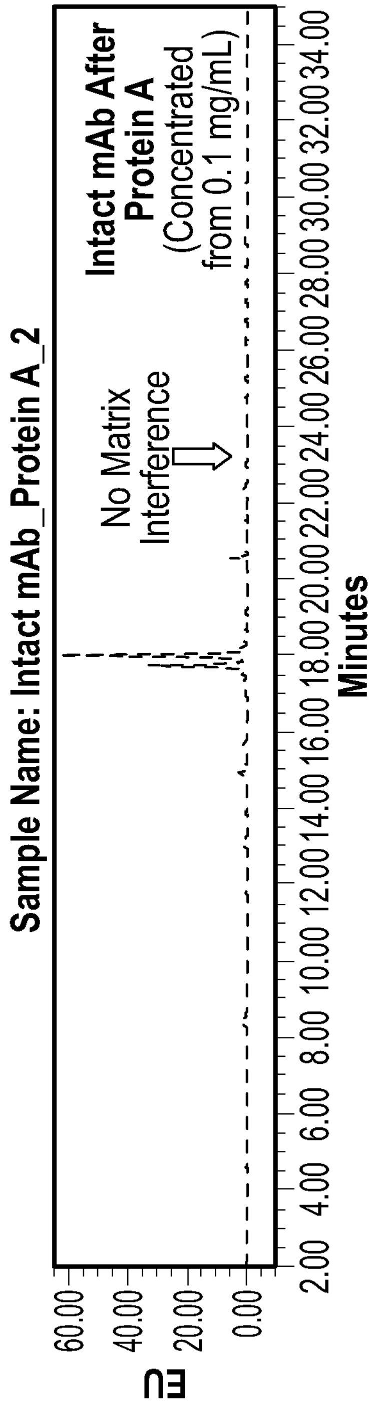
FIG. 1B is a chromatogram showing a glycan profile based on an intact mAb mass check standard produced with Protein A purification.
Figure 2A:
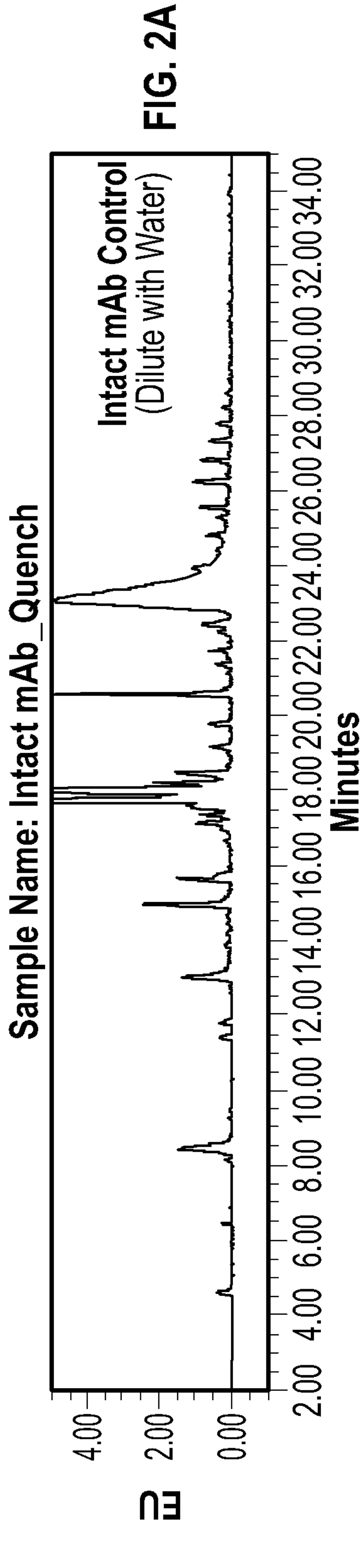
FIG. 2A is an expanded scale of low abundance interference peaks (<5 EU) of the chromatogram of FIG. 1A.
Figure 2B:
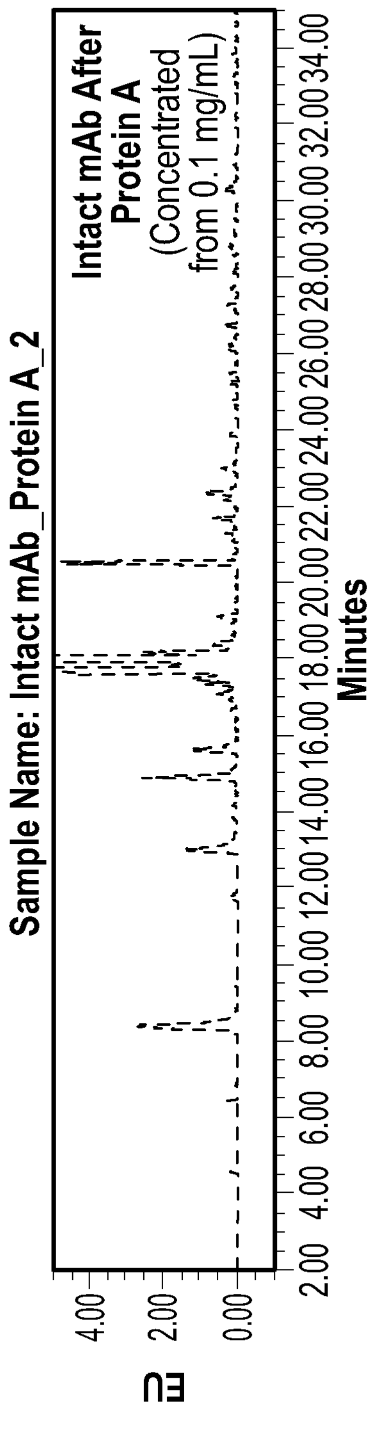
FIG. 2B is an expanded scale of low abundance interference peaks (<5 EU) of the chromatogram of FIG. 1B.

Chromatograms produced by Examples 1-3 are shown in FIG. 1B and FIG. 2B (expanded scale).

Figure 1C:
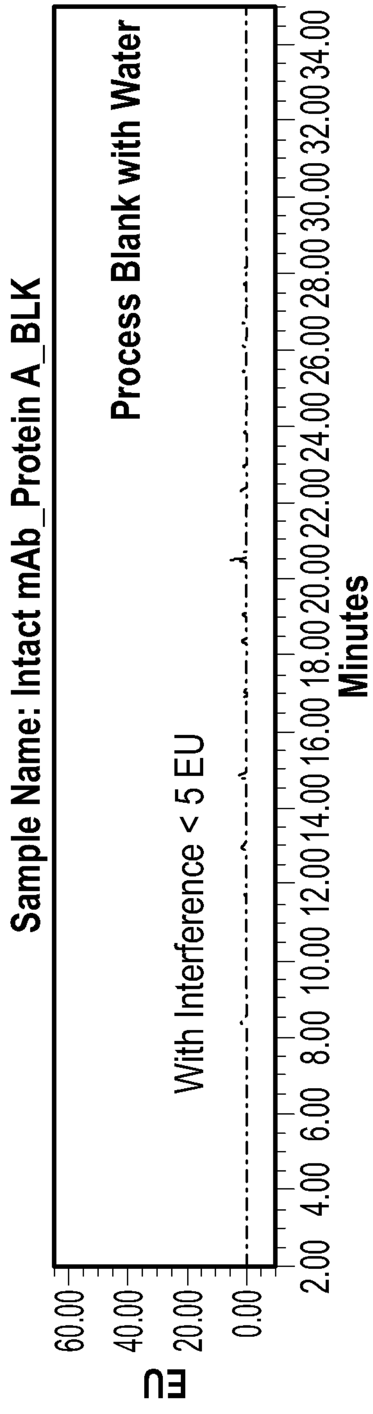
FIG. 1C is a chromatogram produced using water as a process blank.

Chromatograms produced by Examples 2 and 3 (i.e., using unpurified Intact mAb in Example 2 without performing the Protein A purification and enrichment steps of Example 1) are shown FIG. 1A and FIG. 2A (expanded scale). As can be seen by comparing FIGS. 1A-2A with FIGS. 1B-2B, the purification and enrichment steps of procedure A markedly reduced matrix interferences.

Figure 2C:
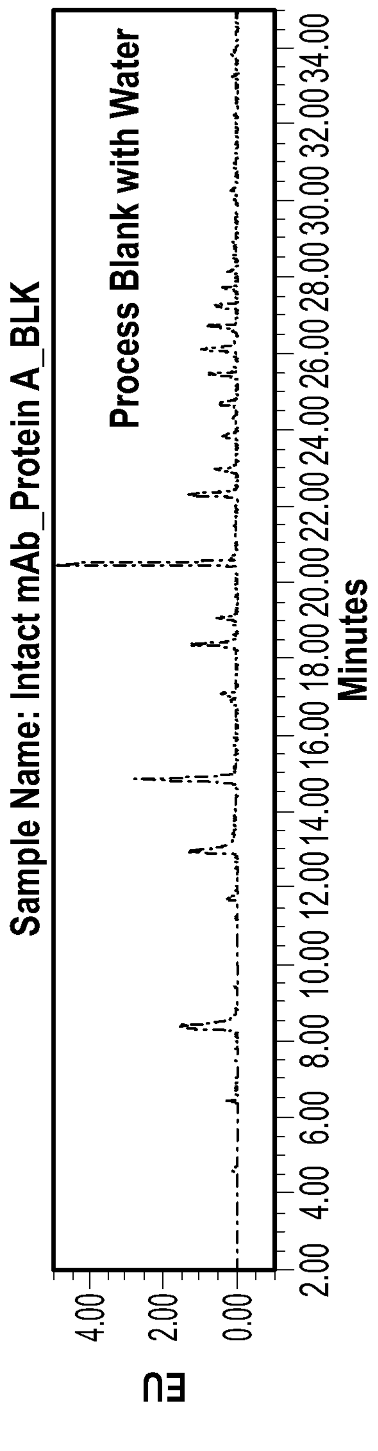
FIG. 2C is an expanded scale of low abundance interference peaks (<5 EU) of the chromatogram of FIG. 1C.

Finally, as a control, the above Examples 1-3 were performed using water as a process blank and the resulting chromatograms are shown FIG. 1C and FIG. 2C (expanded scale).

The invention claimed is:

1. A sample treatment method comprising:

(a) contacting a sample fluid that contains a target antibody with a sorbent that has affinity for the target antibody and separating the sample fluid from the sorbent, thereby forming a sorbent having bound target antibody;

(b) contacting a washing solution that is free of primary amine, secondary amine and thiol groups with the sorbent having bound target antibody and separating the washing solution from the sorbent having bound target antibody, thereby removing unbound molecules from the sorbent having bound target antibody while leaving target antibody bound to the sorbent;

(c) contacting an acidic elution solution that is free of primary amine, secondary amine and thiol groups with the sorbent and separating the elution solution from the sorbent, thereby releasing bound target antibody from the sorbent and forming a first collection fraction that comprises the elution solution and released target antibody;

(d) contacting the sorbent with a neutralization buffer solution that is free of primary amine, secondary amine and thiol groups and separating the neutralization buffer solution from the sorbent, thereby forming a second collection fraction that comprises the neutralization buffer solution;

(e) forming a neutralized solution that comprises the first collection fraction and the second collection fraction, the neutralized solution comprising the released target antibody, the elution solution, and the neutralization buffer solution; and (f) subjecting the neutralized solution to additional processing steps that comprise a chemical reaction with an amine-reactive reagent;

wherein the additional processing steps comprise deglycosylating the released target antibody with a deglycosylating enzyme to form a deglycosylated target antibody and released glycans that comprise released glycosylamines; and reacting the released glycans with a labeling reagent to form labeled glycans.

2. The method of claim 1, wherein the target antibody is selected from an immunoglobulin, a polyclonal antibody, a monoclonal antibody, multivalent antibody, an antibody fragment, an antibody-drug conjugate, or an oligonucleotide-antibody conjugate.

3. The method of claim 1, wherein the elution solution has a pH ranging from 1 to 5.

4. The method of claim 1, wherein the elution solution is further free of hydroxyl groups.

5. The method of claim 1, wherein the elution solution comprises an organic acid that is selected from carboxylic acids and phosphonic acids.

6. The method of claim 1, wherein the neutralization buffer has a pH ranging from 7 to 14.

7. The method of claim 1, wherein the neutralization buffer is further free of hydroxyl groups.

8. The method claim of 1, wherein the neutralization buffer comprises borate anions.

9. The method of claim 1, wherein the sorbent comprises an affinity ligand selected from proteins, antibodies, aptamers, affimers and peptoids.

10. The method of claim 1, wherein, prior to contacting the sample fluid with the sorbent, the method further comprises contacting a binding buffer solution with the sorbent and separating the binding buffer solution from the sorbent, wherein the binding buffer solution is free of primary amine, secondary amine and thiol groups.

11. The method of claim 10, wherein the binding buffer solution has a pH ranging from 5 to 9.

12. The method of claim 10, wherein the binding buffer solution is further free of hydroxyl groups.

13. The method of claim 10, wherein the binding buffer comprises an organic acid anion selected from carboxylates and phosphonates.

14. The method of claim 1, further comprising denaturing the target antibody prior to deglycosylating the target antibody.

15. The method of claim 1, wherein labeling reagent comprises an MS active moiety, a fluorescent moiety, and a moiety that reacts with the released glycans.

16. The method of claim 1, further comprising subjecting the labeled glycans to liquid chromatography to separate the labeled glycans.

17. The method of claim 16, wherein the liquid chromatography is selected from reversed-phase chromatography and hydrophilic-interaction chromatography (HILIC).

18. The method of claim 1, further comprising subjecting the labeled glycans to mass spectrometry and/or measuring a fluorescent signal of the labeled glycans.

* * * * *